US006783988B1

(12) United States Patent
Dinh et al.

(10) Patent No.: US 6,783,988 B1
(45) Date of Patent: Aug. 31, 2004

(54) METHODS FOR QUANTITATIVE AND QUALITATIVE ANALYSES OF PHOSPHOLIPIDS USING ONE-DIMENSIONAL THIN LAYER CHROMATOGRAPHY

(75) Inventors: Tan Thanh Dinh, Fountain Valley, CA (US); Patrice Tremble, Santa Rosa, CA (US); Crystal M. Cunanan, Mission Viejo, CA (US); Christine May Cabiling, Tustin, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 6 days.

(21) Appl. No.: 09/693,186

(22) Filed: Oct. 19, 2000

(51) Int. Cl.$^7$ .......................... G01N 33/92; G01N 30/02
(52) U.S. Cl. .......................... 436/71; 436/161; 436/162; 436/172; 422/70; 210/198.2; 210/198.3; 210/656; 210/658
(58) Field of Search .......................... 436/71, 164, 172, 436/161, 162; 422/70, 82.05, 82.08; 210/656, 658, 198.2, 198.3

(56) References Cited

FOREIGN PATENT DOCUMENTS

WO          99/50655       * 10/1999

OTHER PUBLICATIONS

Dugan "Analysis of Phospholipids by One–Dimensional Thin–Layer Chromatography," Liquid Chromatography vol. 3, No. 2 (Feb. 1985).
Hamilton, et al., "Separation of Neutral Lipid, Free Fatty Acid and Phospholipid Classes by Normal Phase HPLC," LIPIDS, vol. 23, No. 12, pp 1150–1153 (1988).
Lutzke, et al., "An improved method for the identification and quantitation of biological lipids by HPLC using laser light–scattering detection," Journal of Lipid Research vol. 31, pp 2127–2129 (1990).
Shaikh, "Assessment of Various Techniques for the Quantitative Extraction of Lysophospholipids from Myocardial Tissues," Analytical Biochemistry 216, pp 313–321 (1994).
Landi, et al., "HPLC and Light Scattering Detection Allow the Determination of Phospholipids in Biological Samples and the Assay of Phospholipdase $A_2$," Biochemistry and Molecular Biology International vol. 44, No. 6 pp 1157–1166 (May 1998).
Duck–Chong, et al., "Rapid Qualitative Analysis of Polar and Nonpolar Lipids in a Single Sample Using 'Three–Way' Thin Layer Chromatography," Lipids, vol. 18, No. 5 pp 387–389, (1983).

Taki, et al., "TLC Blotting: Application to Microscale Analysis of Lipids and as a New Approach to Lipid—Protein Interaction," Analytical Biochemistry 251, pp 135–143 (1997).
Frederiks, et al., "Separation and Determination of Lipids by One–Dimensional Micro–Thin Layer Chromatography Followed by Denistometry," Journal of Chromatography 150, pp 171–177 (1978).
Schmitz, et al., "A Quantitative Densitometric Method for the Rapid Separtion and Quantitation of the Major Tissue and Lipoprotein Lipids by High–Performance Thin–Layer Chromatogrpahy," Journal of Chromatography 307, pp 65–79 (1984).
Korte, et al., "Phospholipid and Neutral Lipid Separation by One–Dimensional Thin–Layer Chromatography," Journal of Chromatography 232, pp 47–53 (1982).
Entezami, et al., "Analysis of Lipids by One–Dimensional Thin–Layer Chromatography," Journal of Chromatography 387, pp 323–331 (1987).
Yao, et al., "Microanalysis of Complex Tissue Lipids by High–Performance Thin–Layer Chromatography," Analytical Biochemistry 150, pp 111–116 (1985).
Mallinger, et al., "Analysis of Complex Mixtures of Phospholipid Classes from Cell Membranes Using Two–Dimensional Thin–Layer Chromatography and Scanning Laser Densitometry," Journal of Chromatography 614, pp 67–75 (1993).
Folch, et al., "A Simple Method for the Isolation and Purification of Total Lipides From Animal Tissues," Journal of Biological Chemistry, vol. 226, pp 497–505 (1957).
Miwa H. et al., "Thin–layer Chromatography Procedures for Lipid Separation," Journal of Chromatography B: Biomedical Applications, vol. 677, No. 2, (1996) pp 217–223—Abstract.
Touchstone, Joseph C., "Thin–layer Chromatographic Procedures for Lipid Separation," Journal of Chromatography B: Biomedical Applications, vol. 671, No. 1 (1995) pp 183–185—Abstract.

* cited by examiner

Primary Examiner—Maureen M. Wallenhorst
(74) Attorney, Agent, or Firm—Debra D. Condino; Rajiv Yadav

(57) ABSTRACT

A highly sensitive and specific method for the detection and quantification of lipids is provided. Specifically, methods for the simultaneous detection and quantification of phospholipids extracted from mammalian tissues is described. The analytical methods provided disclose a modified one-dimensional thin-layer chromatography technique specifically developed to rapidly and accurantely detect and quantify phospholipids from mammalian cardiac tissues.

22 Claims, 2 Drawing Sheets

METHODS FOR QUANTITATIVE AND QUALITATIVE ANALYSES OF PHOSPHOLIPIDS USING ONE-DIMENSIONAL THIN LAYER CHROMATOGRAPHY

FIELD OF THE INVENTION

The present invention relates to methods for quantitative and qualitative analyses of phospholipids. Specifically, the present invention provides methods of using one-dimensional thin layer chromatography to detect and quantify phospholipids. More specifically, the present invention provides one-dimensional thin layer chromatography methods used to detect and quantify the phospholipid content of mammalian tissues.

DEFINITION OF TERMS

The specification that follows will be more easily understood by reference to the following definitions. Ordinary terms have been used in manners that preserve their traditional meanings. However, there are numerous references to technical aspects of chromatography that require an understanding of specific terms. While these definitions do not deviate substantially for the meanings accepted by those of ordinary skill in the chemical arts, there may be multiple interpretations of the terms used herein. It such cases the following definition of terms prevails.

| | |
|---|---|
| a. Analyte(s): | Compound(s) to be detected in a sample (e.g., lipids present in a tissue extract). |
| b. Column: | A glass or metal tube that is filled with an inert matrix used in high pressure chromatography, gas-liquid chromatography or column chromatography. |
| c. Elution Solvent: | Solvent used to separate components in a mixture. |
| d. Extraction Solvent: | Solvent used to extract the mixture to be analyzed from the naturally occurring milieu. |
| e. Partition: | The process of separating compounds into various phases based on solubility. For example, separating water soluble materials (water soluble phase) from compounds soluble in organic compounds (organic phase) by allowing the respective phases to separate after mixing. |
| f. Resolved: | The process of separating components from a mixture using a chromatographic technique. In thin-layer chromatography resolved refers to the process of separating components from a mixture into discrete, detectable spots. |
| g. Sensitivity: | An assay's limit of detection for a given analyte. |
| h. Specificity: | The assay's ability to discriminate between similar analytes in a sample. |
| i. Spotting: | The process of applying a small amount (microliter quantities) of sample on the chromatographic support's base edge. |
| j. Support: | A thin-layer chromatography plate (glass or plastic) that has been coated with an inert matrix or a sheet of blotter paper in the case of paper chromatography. |

BACKGROUND OF THE INVENTION

Bioprosthetic heart valves (BPHV) have been used since the early 1970s as replacements for diseased human cardiac valves. Originally, the reduced thrombogenicity associated with BPHV made them attractive alternatives to mechanical heart valves. However, BPHV fashioned from bovine pericardium and porcine aortic valves are susceptible to dystrophic calcification. Calcification is associated with approximately 40 to 50 percent of all BPHV failures necessitating re-operation and valve replacement in 10% to 20% of all adult recipients. The calcification rate in children, young adults and acute pathologic conditions is greatly accelerated, consequently, the use of BPHV is limited in these patients.

Recent studies have demonstrated that tissue lipid extraction can significantly reduce calcification, and mineralization generally, in gluteraldehyde cross linked bovine pericardial tissues. This had led some authorities to conclude that lipids act as initiators and/or promoters of tissue mineralization. Therefore, various techniques have been developed to remove lipids from BPHVs prior to implantation. However, in order to monitor and fully understand the role lipids play in minerization of preserved tissues, it is necessary to quantify and qualitate tissue lipid content before, during and after processing. This requires a thorough understanding of lipid chemistry and the problems associated with lipid analytical methods.

Lipids are biological molecules (biomolecules) that are insoluble in water, soluble in organic solvents and are essential components of the plasma membranes that envelop and compartmentalize all living cells. The lipid content of living membranes regulate molecular entry and egress at the cellular and sub-cellular levels. They are found in cell membranes and sub-cellular organelles such as mitochondria, chloroplasts, Golgi bodies, the endoplasmic reticulum and the cell nucleus. In addition to their role as structural components of membranes, lipids serve as energy reserves (triacetylglycerol, also known as neutral fats) and participate in cellular recognition and cell signaling.

There are five major categories of lipids found in biological systems: fatty acids, triacylglycerols, sterols, glycerophopholipids, and sphingolipids. Fatty acids rarely occur in un-complexed, or free forms, in nature. Rather, fatty acids are components of other lipids such as glycerophospholipids, triacylglycerols, and sphingophospholipids. Triacyiglycerols are non-polar (uncharged, hence "neutral fats") fatty acid triesters of glycerol that are synthesized and stored in adipocytes. Adipocytes are "fat cells" that make up the fatty, or adipose, tissue abundant in the subcutaneous tissues of animals that serve as stored energy reserve and provide thermal insulation. Sterols include cholesterol, which are major components of animal cellular and sub-cellular membranes. Sterols occur in much lower concentration in plants and have not been identified in bacterial (prokaryotic) cell membranes. Moreover, cholesterol is an essential precursor to steroid hormones.

Glycerophospholipids (phosphoglycerides) are the most common lipids associated with cell membranes. The simplest phosphoglyceride is phosphatidic acid (A) which is relatively scarce in cell membranes; however, phosphatidic acid can serve as a precursor for all major phosphoglycerides including phosphatidylcholine (PC), phosphatidylserine (PS), phosphatidylinositol (PI), phosphatidylglycerol (PG), phosphatidylethanolamine (PE) and diphosphatidylglycerol (also known as cardiolipin and found primarily in mitochondrial membranes). *Biochemistry* Voet and Voet; *Lipid Metabolism*; pages 663–726; John Wiley and Sons, New York, 2000. Sphingophospholipids include sphingomyelins (SM) and are a principle component of nerve cell myelin sheaths. Sphigophospholipids (SP) have similar conformations and charge distribution to glycerophospholipids and include the phosphorylated head group associated with glycerophospholipids. Consequently, there is considerable chemical similarity between glycerophospholipids and sphigophospholipids; as a result they will be referred to herein collectively as "phospholipids" for convenience.

Phosphatidylcholine, phosphatidylserine, phosphatidylethanolamine, phosphatidylinositol, phosphatidylglycerol, cardiolipin and sphingophospholipids are generally the most abundant phospholipids found in pericardial tissues. It has been reported that phosphatidylserine, cardiolipin and phosphatidylinositol play significant roles in mineralization (D)alas, E. Ioannou, P. V. and P. G. Koutsoukos, In Vitro *Calcification: Effect of Molecular Variables of the Phospholipid Molecule.* 1990. American Chemical Society. Vol 6:3 535–538). Therefore, it is essential that any analytical method used to assess tissue lipid content have equal sensitivity and specificity for all phospholipids. Phospholipids possess many chemical similarities that make their physical separation from tissue extracts challenging. One of the most effective techniques for separating complex mixtures of large organic compounds, including phospholipids, is chromatography.

Mikhail Semenovich Tswett ("Tswett"), a Russian botanist, developed chromatography (from the Latin for color writing) shortly after the turn of the twentieth century. Tswett was studying plant pigments and developed the technique of column adsorption chromatography by passing plant extracts through glass columns packed with calcium carbonate (chalk). The different pigments (each a separate organic compound) separated into discrete bands within the packed calcium carbonate column. The subtle differences in molecular weight, shape and charge between the pigments determined the rate that the plant pigment mixture (liquid or mobile phase) moved through the calcium carbonate column (solid support, or stationary phase). Today there are numerous variations on Tswett's original column chromatography procedure that are based on the general principle described above. These include gas chromatography (or more specifically gas-liquid partition chromatography-GC and GLC), high-pressure liquid chromatography (HPLC), paper chromatography and thin layer chromatography (TLC).

In gas chromatography the sample containing the mixture to be separated is heated to temperatures needed to vaporize the mixture's components. An inert gas such as nitrogen or helium carries the vaporized mixture (the mobile phase) into a column. The column is packed with a finely divide inert solid that is coated with another liquid of low volatility (the stationary phase). The vaporized compounds in the mobile phase move through the column at different rates due to the compounds' different relative solubilities in the stationary phase (liquid) and the gas phase (a phenomenon referred to as partitioning). Gas-liquid chromatography is one of the most commonly used analytical techniques; however, it cannot separate complex mixtures of phospholipids.

High-pressure liquid chromatography is a superb analytical tool that relies on the basic principles of column chromatography. Samples are dissolved in a suitable solvent mixture (the mobile phase) and the passed through extremely high surface area capillary silanized silica columns (stationary phase) under tremendous pressure. The components of the mobile phase (the solvent mixture) change over time forming a gradient. Samples elude through the gradient at different intervals based on their charge, molecular weight and relative solubility in the solvent gradient. Various forms of detectors are placed at the end of the column to record each compound's passing.

Early BPLC columns operated within a narrow pH range and were thus not versatile enough to separate complex lipid mixtures. Moreover, ultraviolet light detection systems were notoriously insensitive and not suited for lipid quantitation. However, recent improvements in derivatized silanized silica columns have resulted in stable supports that operate in a broad pH range (1–12) making them more useful for lipid analysis and laser fight scattering detection systems have significantly improved HPLC lipid quantitation sensitivity.

However, BPLC still presents two major drawbacks. Fist, HPLC is a linear system. One sample is injected at a time, multiple sample analysis remains tedious and time consuming even using auto-injectors. Moreover, HPLC is expensive and complex to operate. Hundreds of thousands of dollars are required to properly equip a fully functional HPLC laboratory and train personnel. If multiple BPLC systems are added to expedite sample processing, the costs go up considerably. Consequently, HPLC facilities that can rapidly process complex lipid containing samples are limited and the cost per sample is extremely high.

Thin layer and paper chromatographies are based on similar principles. A sample containing the compounds to be separated is dissolved in a suitable extraction solvent and a small aliquot is placed near the edge at the support's base. After the sample spot dries, the support is placed in a container (developing chamber) with sufficient elution solvent to come to a level below the spot. The solvent migrates up the support carrying the compounds in the sample with it at different rates. This procedure is extremely versatile, inexpensive to perform and a number of samples and standards can be resolved simultaneously. When the samples are run in one direction, i.e. up the support, the procedure is referred to as one-dimensional chromatography. This is by far the easiest chromatography method to perform and provides the highest sample throughput.

However, molecules having a high degree of similarity in molecular weight, charge and molecular shape, such as phospholipids, could not be separated using one-dimensional chromatography and were generally not compatible with the cellulose fiber matrix used in paper chromatography. Consequently, a variation on one-dimensional TLC known as two-dimensional TLC was developed. Samples are loaded onto the support and resolved as described above for one-dimensional TLC. After the samples have resolved, the TLC plate is turned 90 degrees and placed in another developing chamber containing a different elution solvent. After the samples have resolved in the second direction, the spots are further separated making the identification of complex, highly similar compounds possible. However, two-dimensional TLC is time consuming and requires that a single TLC plate be resolved twice. This considerably limits the number of samples and standards that can be run simultaneously.

Recently, E. A. Dugan reported the separation of PG, PE, PS, PI PC and SM using one-dimensional thin-layer chromatography (the "Dugan method") (Dugan, E. A., *Analysis of Phospholipids by One-Dimensional Thin-Layer Chromatography.* 1985. Liquid Chromatography, Volume 3 Number 2). However, the Dugan method does not provide the degree of separation and reproducibility necessary for precise quantitation of phospholipid samples. Moreover, the Dugan method was particularly insensitive for the separation of PC and SM, and PC was not adequately resolved using the methods disclosed therein.

Therefore, there remains a need for an inexpensive, high through-put, accurate analytical process suitable for the simultaneous qualitative and quantitative analysis of lipids in extracted tissue samples.

SUMMARY OF THE INVENTION

It is an object of the present invention to provide a rapid, cost effective and reproducible quantitative method for determining the phospholipid content of a sample.

It is another object of the present invention to provide a rapid, cost effective and reproducible quantitative method for determining the phospholipid content of tissue extracts.

It is another object of the present invention to provide a rapid, cost effective and reproducible quantitative method for determining the phospholipid content of tissue extracts using one-dimension thin layer chromatography.

It is an object of the present invention to provide a rapid, cost effective and reproducible qualitative method for determining the phospholipid content of a sample.

It is another object of the present invention to provide a rapid, cost effective and reproducible qualitative method for determining the phospholipid content of tissue extracts.

It is another object of the present invention to provide a rapid, cost effective and reproducible qualitative method for determining the phospholipid content of tissue extracts using one-dimension thin layer chromatography.

It is yet another object of the present invention to provide a rapid, cost effective and reproducible method for the simultaneous qualitative and quantitative determining the phospholipid content of tissue extracts using one-dimension thin layer chromatography.

The present invention generally provides methods for the qualitative and quantitative analysis of biological samples containing mixtures of lipids, specifically mixtures containing neutral lipids and phospholipids. Samples are extracted using organic solvents (extraction solvent), partitioned, dried and the lipid fraction redissolved in an extraction solvent as known to those skilled in the art. The samples are then applied to activated thin layer chromatography plates. Next, the plates are equlibrated and resolved using the elution solvent of the present invention. The resolved plates are stained with a fluorescent dye and then scanned using fluorescent imaging and quantified using appropriate software.

In one embodiment the present invention is used to determine the lipid content of mammalian cardiac tissues. Samples are extracted using a methanol-chloroform solution and processed using silica gel coated thin layer chromatography plates. The lipids are developed using a chloroform, methanol, acetic acid, aqueous potassium chloride solution and detected using primulin and a Storm® imaging unit.

The method of the present invention provides a technique to qualitate and quantify phosphatidylcholine, phosphatidylethanolamine, phosphatidylinositol, phosphatidic acid, phosphatidylserine, sphingomyelin and phosphatidylglycerol present in a single tissue extract. Neutral lipids do not separate from the elution solvent of the present invention and migrate out of the mixture with the solvent front (the leading edge of the solvent as it migrates up the chromatography plate). Consequently, the presence of neutral lipids in tissue samples does not interfere with phospholipid detection quantitation.

Other objects, features and advantages of the present invention will be apparent to those skilled in the art from a consideration of the following detailed description of preferred exemplary embodiments thereof taken in conjunction with the Figure which will first be briefly described.

DETAILED DESCRIPTION OF THE INVENTION

Figure 1:
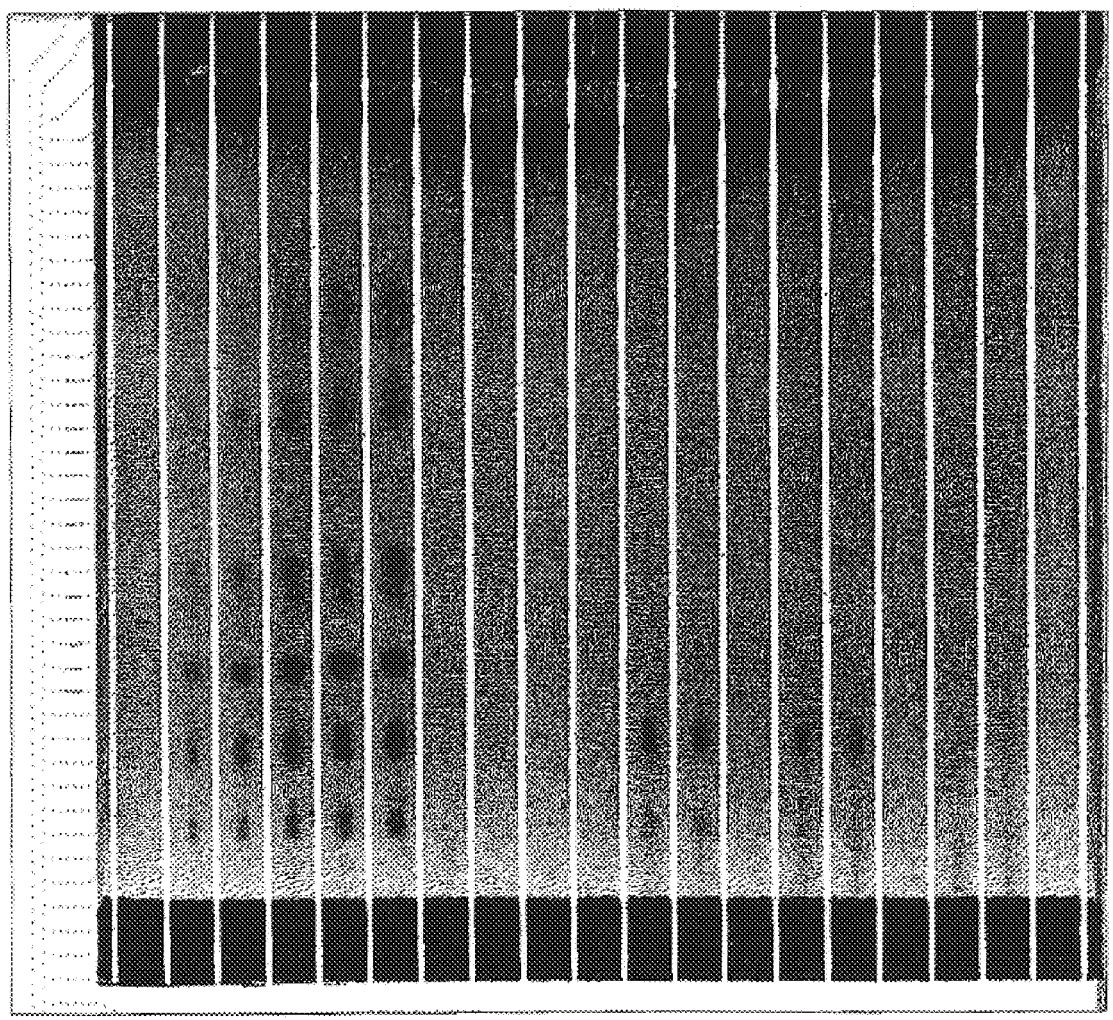
FIG. 1 depicts a resolved TLC support demonstrating the high degree of analyze spot separation and the minimum streaking and smearing that occurs when one-dimensional TLC analysis of cardiac tissue extracts is performed in accordance with the teachings of the present invention.

Naturally occurring mixtures of biomolecules present significant challenges to analytical chemists seeking to isolate and identify their individual constituents. This is particularly true for cellular extracts that contain mixtures of large complex compounds such as proteins, nucleic acids and lipids. Prior to 1900 the majority of all chemical purification and separation techniques relied on chemical extraction, fractional distillation, crystallization and re-crystallization. These techniques generally rely on differences in melting points, boiling points, and solubility in various solvents to separate and identify different chemical species. Such methods are tedious, result in low yields, lack reproducibility and are not suited for quantitative analysis when samples contain numerous closely related compounds.

At the turn of the twentieth century techniques emerged that separated biomolecules from each other based on a molecule's weight, shape, and charge. These methods, known as chromatography (Latin for "color writing"), principally rely on differential solubility or absorption of compounds to separate molecules between a stationary phase and a mobile phase. Chromatographic mobile phases are liquids that dissolve the molecules of interest consisting primarily of low molecular weight organic solvents such as alcohols, ketones, aldehydes, and aromatic compounds. Stationary phases are generally inorganic or organic complexes that are insoluble in the solvents including chalks, silicates, cellulose, argarose and acrylates. (The preceding definition of "mobile and stationary phases" does not apply to gas-liquid chromatography—GLC. In GLC the mobile phase is an inert gas and the stationary phase is an organic solvent.)

Simple methods for performing chromatographic separation involve dissolving a sample containing compounds to be separated in a suitable extraction solvent. The sample is then applied as a small spot (spotting) to the base of a solid stationary phase, or support. The sample is allowed to dry and the very bottom of the support (below the sample spot) is suspended in the elution solvent. The elution solvent will migrate up the support carrying the compounds contained in the spot with it. Different compounds in the spot will move with the elution solvent at different rates depending on their individual solubilities in the elution solvent and their relative interactions with the support matrix. Larger molecules will generally move more slowly than smaller ones, charged molecules may bind to oppositely charged portions of the support and their migration will be retarded, and insoluble compounds will generally not migrate at all.

Once the elution solvent has migrated up the paper the chromatographic process is complete and the support is removed from the solvent and dried. The support matrix is then exposed to a suitable chemical or physical process that permits visualizing the migrated compounds. The distance a compound traveled from its original spot is measured in centimeters and is divided by the distance the solvent traveled. This value, an $R_f$, is generally unique for every compound thus providing a rapid and relatively simple means of separating and identifying a great number of compounds. This particular technique is called one-dimensional chromatography because the sample is allowed to migrate in just one direction.

However, there are compounds that behave so similarly in a particular elution solvent and/or interact with the stationary phase in near identical fashion such that they migrate as a single spot. In these cases the compounds can be further separated using multi-dimensional chromatography (two or three-dimensions) can be used. Generally, this involves rotating the stationary phase 90 degree on its axis following the completion of the first migration and using a second, different elution solvent. The molecules' interactions with the new elution solvent/stationary phase combination is different than the first system resulting in detectable separation. However, only one sample can be run per support (TLC plate) using two-dimensional chromatography. Moreover, quantitative techniques are less accurate because separate TLC plates must be used for each sample and another for the standards. As a result, subtle changes in the reaction conditions between the various TLC plates can cause a slight difference in assay resolution.

The sensitivity and specificity of TLC is determined by a number of factors including the constituents of the mobile phase, the charge and molecular size of the stationary phase and environmental conditions including temperature and humidity. Changes in the mobile phase solvent concentrations, pH, and polarity can have dramatic effects on the assay's resolving capacity. The present inventors have surprisingly discovered that the separation of lipids using one-dimensional TLC can be significantly enhanced using the elution solvent of the present invention.

Analyte detection is another important factor that must be optimized to provide maximum detection sensitivity and reproducibility. Analytes are generally detected in a sample after the TLC plate has been resolved and dried. Liquid detection reagents that interact with the analytes are applied to the surface of the dried plate. Non-limiting examples of detection reagents include acidic cupric salts, ninhydrin, molybdenum blue reagent, and fluorescent dyes, including but not limited to primulin. Cupric salts are non-specific charring reagents that bind to the sample and turn various shades of brown upon heating to between approximately 170° C. to 180° C., ninhydrin and molybdenum react with free amino groups forming a chromogenic complex with the analyze, and fluorescent dyes intercalate with the analyze and emit a detectable UV wavelength in response to an activating UV light source. The degree of charring, chromogenic development or UV emission is generally proportional to the amount of analyze present in the sample.

Sample analysis generally begins with extracting the compounds to be assayed from their naturally occurring milieu. For example, the lipids assayed using the teachings of the present invention are naturally found in tissue samples, specifically cardiac tissue samples. In the present invention, porcine and bovine cardiac tissues are first extracted using one or more organic solvents that are compatible with amphiphilic compounds such as phospholipids. Amphiphilic compounds are molecules that possess both charged (polar) and uncharged (non-polar) regions. The phosphate containing head of phospholipids are generally charged and the fatty acid tail is uncharged. These compounds are usually more soluble in non-polar solvents than polar ones; however, adding small amounts of a polar solvent to the non-polar solvent (known as polar modification) can increase solubility of many amphiphilic compounds.

In the present invention the inventors have found that the maximum lipid extraction from tissue homogenates is generally achieved using extraction solvent mixtures such as, but not limited to, chloroform and methanol. In one embodiment of the present invention a mixture containing chloroform (Mallinckrodt Baker, Inc., Phillipsburg, N.J.) and methanol (Mallinckrodt Baker) was used to extract porcine and bovine cardiac tissue using a modification of Foich et al. (Folch, J. et al. 1957. *A Simple Method for the Isolation and Purification of Total Lipids from Animal Tissue*. J. Biol. Chem., 226: 497–505, the entire contents of which is herein incorporated by reference).

Specifically, fresh pericardium (sample) that had been crushed in liquid nitrogen is added to a 2:1 mixture of chloroform and methanol (extraction solvent). The sample/extraction solvent mixture is purged with nitrogen gas, sealed in a glass tube and extracted at ambient temperature for approximately 6.5 hours. Next, an appropriate volume of physiological saline (aqueous phase) is added to the sample/solvent mixture and thoroughly mixed. Insoluble materials including tissue fragments and coagulated proteins were removed along with the aqueous phase and the solvent is evaporated to dryness under a stream of nitrogen gas. Extracted lipids are reconstituted in chloroform and stored at or below −75° C. until processed further.

In one embodiment of the present invention samples to be analyzed and standards are spotted onto TLC plates that have been pre-activated using methods known to these skilled in the art. Generally, TLC plates are activated by heating to dryness and then cooling in an anhydrous environment. In one embodiment of the present invention the TLC plates are pre-activated HPTLC-HL plates (Analtech, Inc., Newark, Del.). Samples are spotted using a micropipet being careful not to overload the plate with sample. Overloading a TLC plate can result in smearing of the analyte which significantly reduces the assay's sensitivity and specificity. Samples are best applied in small amounts letting each drop completely dry before applying the next. For best results, it is important that the spot be small and intense. Generally, applying repeated, small droplets to the same place helps to assure small, intense spots. Next the spotted plate is placed in an oven to assure that the spots are completely dried. In one embodiment of the present invention the plates are dried using a laboratory hot-cold drier using alternating cycles of hot and cold air.

After the spots are thoroughly dried, the plates are equilibrated by suspending them in a tank containing sufficient elution solvent to saturate the environment therein. Care is taken not to allow the plate to contact liquid elution solvent. After a suitable equilibration period the plates are lowered into the elution solvent with the solvent level just below the sample spot. The plates are then resolved for a time sufficient to allow the elution solvent to migrate up the entire plate stopping just before its upper edge. At the conclusion of the resolving period the plates are removed from the elution solvent tank and dried.

Analytes are detected by exposing the dried resolved plates toga suitable detection regent. In one embodiment of the present invention the detection reagent is a fluorescent dye such as, but not limited to, primulin. The fluorescent detection reagent is applied as an aerosol to the dried TLC plate. The plates are then dried and read. Lipids present in the sample will react with the fluorescent dye forming a fluorescent complex that will emit a specific wavelength of UV light in response to an activating wavelength in the ultraviolet region. In one embodiment of the present invention a semi-automated TLC plate scanner such as, but not limited to, a Molecular Dynamics, Sunnyvale, Calif., Storm® PhosphorImager® system is used. Data are collected and analyzed using a microprocessor having quantitative software therein such as, but not limited to, ImageQuant®.

Figure 2:
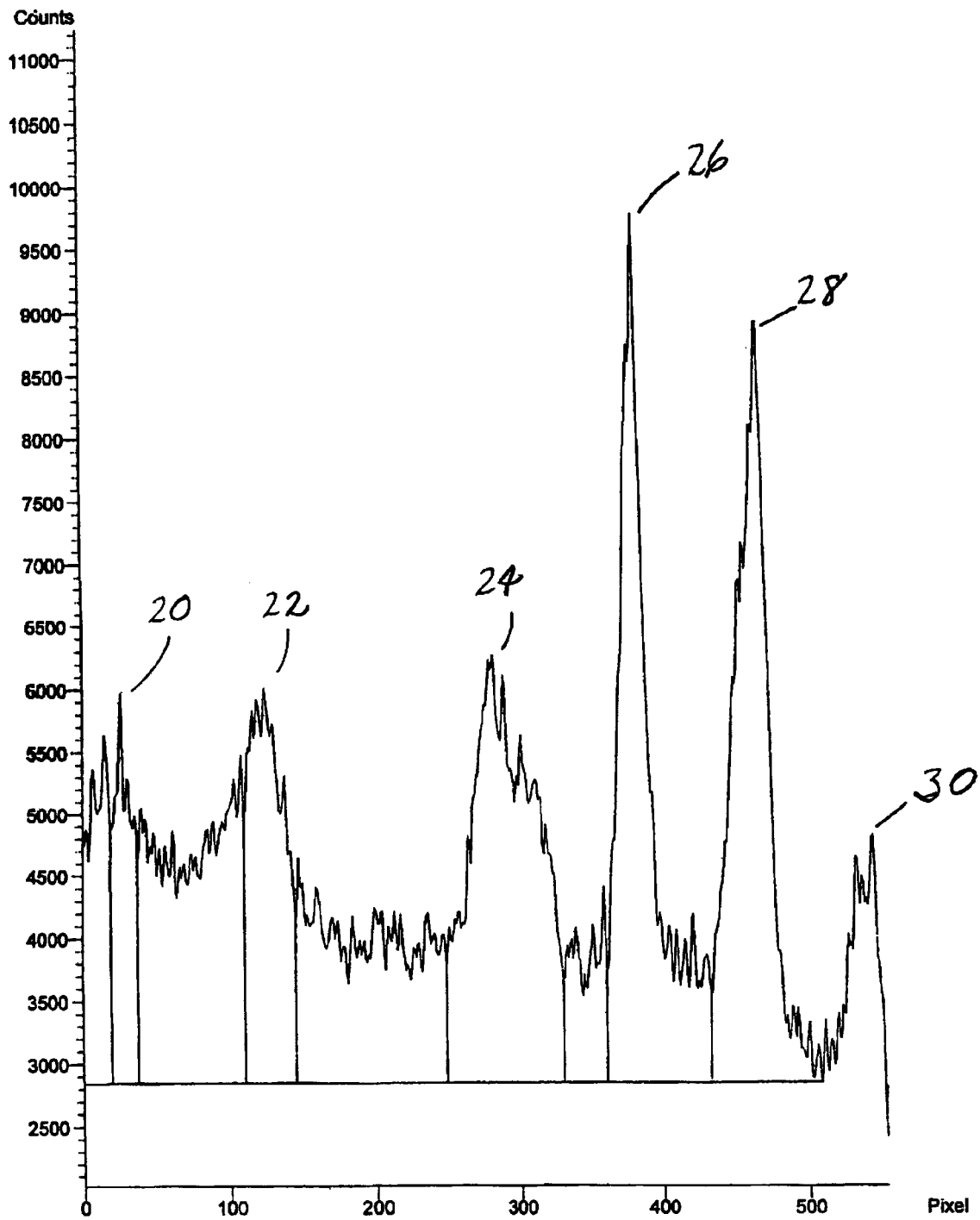
FIG. 2 graphically depicts phospholipid separation obtained using the methods of the present invention. The graphs depicted in FIG. 2 were obtained by scanning the developed TLC supports using the Molecular Dynamics Storm® PhosphorImager® ImageQuant® (Molecular Dynamics, Inc.) analytical software.

The most important aspect of quantitation is the degree of separation and tightness of the analyte spots following resolution. Analyte spots that are streaked or smeared and those that are overlapping onto adjacent analytes cannot be accurately quantified. FIG. 1 demonstrates the excellent resolution that is achieved using the teachings of the present invention. FIG. 2 graphically depicts the results obtained when a mixture containing 0.2 µg/mL each of L-α-Phosphatidic Acid 20, L-α-Phosphatidylethanolamine 22, L-α-Phosphatidylserine 24, L-α-Phosphatidylinositol 26, L-α-Phosphatidylcholine 28, and Sphingomyelin 30 is resolved using the teaching of the present invention and the developed TLC plate is scanned using the Molecular Dynamics Storm® PhosphorImager® ImageQuant® (Molecular Dynamics, Inc.) analytical software.

EXAMPLES

Preparation of Cardiac Tissues Extracts a. Excise excess fat from a piece of fresh bovine pericardium or porcine aortic valve, mince the remaining tissue with a scalpel keeping the tissue submerging in ice cold saline.
b. Immerse the minced, de-fatted tissue in sufficient liquid nitrogen to cover the entire tissue section. Carefully pulverize the frozen tissue and weigh the sample.
c. Transfer the weighed, pulverized tissue sample to a glass vial and store at approximately −80° C. until processed further.
d. Prepare an extraction solvent mixture containing two parts Chloroform, Mallinckrodt Baker HPLC grade or equivalent and one part Methanol, Mallinckrodt Baker HPLC grade or equivalent. Mix well and store under a reduced atmosphere.
e. Add approximately 1 gram defatted pulverized tissue to 7 to 10 mL of extraction solvent. Gas-out the sample vial containing the tissue and extraction solvent and seal. Mix thoroughly for approximately six hours at room temperature.
f. Add a volume of physiological saline equal to approximately 20% of the sample volume and continue mixing for an additional thirty minutes.
g. The mixed samples are then centrifuge for 20 minutes at approximately 2,000×g or a force sufficient to remove the bulk tissue and precipitated proteins.
h. Allow the phases to separate and remove the solvent phase containing the extracted lipids.
I. Place the extraction solvent phase in a tared vessel and evaporate the sample to dryness under a gentle stream of inert gas. Store dried lipids at or below approximately −75° C.

Quantitative and Qualitative Phospholipid Analysis Using One-dimensional Thin-layer Chromatography Required Equipment
Pre-activated TLC plates, Uniplate HPTLC-HL Analtech.
Required Materials
a. Pre-aliquoted phospholipid standards and samples needed for testing:
  1. L-α-Phosphatidylcholine Avanti Polar Lipid, Inc. (Alabaster, Ala.)
  2. L-α-Phosphatidylethanolamine Avanti Polar Lipid, Inc.
  3. L-α-Phosphatidylinositol Avanti Polar Lipid, Inc.
  4. Sphingomyelin Avanti Polar Lipid, Inc.
  5. L-α-Phosphatidic Acid Avanti Polar Lipid, Inc.
  6. L-α-Phosphatidylserine Avanti Polar Lipid, Inc.

While the aforementioned lipid standards were acquired from Avanti Polar, Inc., it is understood that one of ordinary skill in the art would know other sources for suitable equivalents.
b. Chloroform, Mallinckrodt Baker HPLC grade.
c. Methanol, Mallinckrodt Baker HPLC grade.
d. Acetic Acid, glacial, Mallinckrodt Baker.
e. Purified water
f. Potassium chloride, Mallinckrodt Baker.
g. Pre-made 0.05% primulin working solution in glass sprayer with air attachment or other suitable apparatus for producing a fine primulin aerosol (Sigma Chemicals, St. Louis, Mo.).

Analytical Method
A. Spotting Standards and Samples
  1. Remove necessary aliquots of phospholipid standards and samples from frozen storage and allow to thaw to room temperature.
  2. Lightly label each plate with a pencil on the top absorbent strip of the plate with the date and some unique identification, i.e., "A" or "B." Label each lane with the appropriate concentration; start with the sample or standard having the lowest concentration and move to those having the highest concentration. Work from left to right. Samples are spotted in duplicate or triplicate. Skip the lanes on the left and right edges of the plate.
  3. Ensure the standards and samples have warmed to room temperature and are well mixed. Spot the samples and standards being careful to ensure small, tight spots.
  4. When all standards and samples have been applied the plates were dried.
B. Solvent Preparation
  1. Prepare a stock solution of 2.5% potassium chloride (KCl) in purified water.
  2. Prepare the elution solvent in a fume hood in glass containers according to the following ratios:

| Chloroform: | Methanol: | Acetic Acid: | water with 2.5% KCl |
|---|---|---|---|
| 35 : | 10 : | 9.8 : | 1.2 |

3. Mix the elution solvent well and de-gas it.
Assay Equilibration
  1. Load plates into the chromatography rack, spot side down. Place the rack and plates into the tank and replace the tank lid. Verify that the lid is in place to prevent air from entering the tank during the tank equilibration.
  2. Allow the rack and plates to hang in the tank for equilibration.
Resolving Method
  1. After the plates have been fully equilibrated gently lower them into the elution solvent so that the solvent level is below sample and standard spots.
  2. Allow the standards and samples on the TLC plates to resolve until the migrating solvent front is approximately 5 mm from the bottom of the top absorbent strips on the TLC plate, remove the plates from the solvent tanks. Allow the plates to air dry.
Analyte Detection
  1. After the plates are dried spray the plates evenly with primulin solution.
  2. After all plates have been stained, dry the plates again.

3. Load dried TLC plate into the Molecular Dynamics Storm® PhosphorImager® (or equivalent UV scanner) and scan plate. Print out sample and standard curved with using the ImageQuant® (Molecular Dynamics, Inc.) analytical software.

From the foregoing description, one skilled in the art can readily ascertain the essential characteristics of the invention and, without departing from the spirit and scope thereof, can adapt the invention to various usages and conditions. Changes in the form and substitution of equivalents are contemplated as circumstances may suggest or render expedient, and although specific terms have been employed herein, they are intended in a descriptive sense and not for purposes of limitation. Furthermore, any theories attempting to explain the mechanism of actions have been advanced merely to aid in the understanding of the invention and are not intended as limitations, the purview of the invention being delineated by the following claims.

We claim:

1. A method for the simultaneous quantitative and qualitative determination of individual phospholipids in a phospholipid mixture, wherein said phospholipid mixture comprises a neutral lipid, said method comprising:

dissolving said phospholipid mixture in at least one extraction solvent;

applying said at least one extraction solvent having said phospholipid mixture dissolved therein to a thin layer chromatography (TLC) plate;

placing said TLC plate having said phospholipid mixture applied thereto into an elution solvent mixture comprising chloroform, methanol, acetic acid, and an aqueous solution of potassium chloride; and allowing said phospholipid mixture to migrate up said TLC plate in one direction until said individual phospholipids are resolved into discrete, detectable spots such that all said individual phospholipids present in said phospholipid mixture can be individually detected and said discrete detectable spots are separately quantifiable.

2. The method of claim 1 wherein said individual phospholipids are selected from the group consisting of phosphatidylcholine, phosphatidylethanolamine, phosphatidylinositol, phosphatidic acid, phosphatidylserine, and sphingomyelin.

3. The method of claim 1 wherein said at least one extraction solvent is selected from the group consisting of chloroform, methanol, and water.

4. The method of claim 3 wherein said at least one extraction solvent comprises chloroform and methanol.

5. The method of claim 4 wherein said at least one extraction solvent comprises two parts chloroform and one part methanol.

6. The method of claim 1 wherein said TLC plate is coated with a silica gel.

7. The method of claim 1 wherein said aqueous solution of potassium chloride consists essentially of water and 2.5% potassium chloride.

8. The method of claim 1 wherein said elution solvent mixture consists essentially of 35 parts chloroform, 10 parts methanol, 9.8 parts acetic acid and 1.2 parts aqueous solution of potassium chloride.

9. The method of claim 1 further comprising detecting said individual phospholipids using an ultraviolet detection system.

10. The method of claim 9 wherein said ultraviolet detection system further comprises primulin.

11. A method for the quantitative determination of individual phospholipids in a phospholipid mixture, wherein said phospholipid mixture comprises a neutral lipid, said method comprising:

dissolving said phospholipid mixture in at least one extraction solvent;

applying said at least one extraction solvent having said phospholipid mixture dissolved therein to a thin layer chromatography (TLC) plate;

placing said TLC plate having said phospholipid mixture applied thereto into an elution solvent mixture comprising chloroform, methanol, acetic acid, and an aqueous solution of potassium chloride; and allowing said phospholipid mixture to migrate up said TLC plate in one direction until said individual phospholipids are resolved into discrete, detectable spots such that all said individual phospholipids present in said phospholipid mixture can be individually detected and said discrete detectable spots are stately quantifiable.

12. The method of claim 11 wherein said individual phospholipids are selected from the group consisting of phosphatidylcholine, phosphatidylethanolamine, phosphatidylinositol, phosphatidic acid, phosphatidylserine, and sphingomyelin.

13. The method of claim 11 wherein said at least one extraction solvent is selected from the group consisting of chloroform, methanol, and water.

14. The method of claim 11 wherein said at least one extraction solvent comprises chloroform and methanol.

15. The method of claim 14 wherein said at least one extraction solvent comprises two parts chloroform and one part methanol.

16. The method of claim 11 wherein said TLC plate is coated with a silica gel.

17. The method of claim 11 wherein said aqueous solution of potassium chloride consists essentially of water and 2.5% potassium chloride.

18. The method of claim 11 wherein said elution solvent mixture comprises 35 parts chloroform, 10 parts methanol, 9.8 parts acetic acid and 1.2 parts aqueous solution of potassium chloride.

19. The method of claim 11 further comprising detecting said individual phospholipids using an ultraviolet detection system.

20. The method of claim 19 wherein said ultraviolet detection system further comprises primulin.

21. A method for the simultaneous quantitative and qualitative determination of individual phospholipids in a phospholipid mixture, said method comprising:

dissolving said phospholipid mixture in at least one extraction solvent;

applying said at least one extraction solvent having said phospholipid mixture dissolved therein to a thin layer chromatography (TLC) plate;

placing said TLC plate having said phospholipid mixture applied thereto into an elution solvent mixture comprising chloroform, methanol, acetic acid, and an aqueous solution of potassium chloride; and allowing said phospholipid mixture to migrate up said TLC plate in one direction until said individual phospholipids are resolved into discrete, detectable spots such that all said individual phospholipids present in said phospholipid mixture can be individually detected and said discrete detectable spots are separately quantifiable.

22. The method of claim 21, wherein said phospholipid mixture includes a neutral lipid.

* * * * *